United States Patent [19]

Newman et al.

[11] Patent Number: 4,687,736

[45] Date of Patent: Aug. 18, 1987

[54] DETECTION OF BIOLOGICAL SUBSTANCES BY SPECIFIC LABELLING TECHNIQUES

[75] Inventors: Goeffrey R. Newman, Rhoose; Bharat Jasani, Penarth; Edward D. Williams, Boverton, all of United Kingdom

[73] Assignee: The University of Wales College of Medicine, Cardiff, United Kingdom

[21] Appl. No.: 666,679

[22] Filed: Oct. 31, 1984

[51] Int. Cl.[4] .......................... C12Q 1/68; C12Q 1/28; G01N 33/53; G01N 33/566

[52] U.S. Cl. ............................................. 435/7; 435/6; 435/28; 436/501; 436/518; 436/827

[58] Field of Search ....................... 436/501, 518, 827; 423/DIG. 17; 75/118 R, 118 P; 435/6, 7, 28

[56] References Cited

U.S. PATENT DOCUMENTS 4,508,820  4/1985  Merril et al. ......................... 435/29

OTHER PUBLICATIONS

Putt, F. A., Manual of Histopathological Staining Methods (1972) (Wiley & Sons, Pub.) pp. 278–279.
Jones, P. P., (1977) Journ. of Exp. Med. 146:1261–1279.
Oakley, B. et al., (1980) Anal. Biochem 105:361–63.

*Primary Examiner*—Sidney Marantz
*Assistant Examiner*—Jack Spiegel
*Attorney, Agent, or Firm*—Young & Thompson

[57] ABSTRACT

This invention relates to the detection of biological substances and is particularly though not exclusively applicable to labelling techniques employing antibodies or other specific binding agents. Thus the invention consists in a method for the detection of a biological substance of interest (optionally in an environment of biological cells) in which a marker substance is linked specifically, directly or indirectly, to the substance of interest, the marker substance being selected to act as a catalyst in a subsequent process of reduction of silver using a developing solution.

18 Claims, No Drawings

DETECTION OF BIOLOGICAL SUBSTANCES BY SPECIFIC LABELLING TECHNIQUES

This invention relates to the detection of biological substances and is particularly though not exclusively applicable to labelling techniques employing antibodies or other specific binding agents.

The term "detection" as used herein is to be understood to include all related procedures, including identification, amplification, localization, quantification, or the like.

· The invention is particularly concerned with the problems involved in producing the optimum signal, particularly though not exclusively an optical or visual signal, at the site of the substance to be detected.

Accordingly it is an object of the invention to provide a highly sensitive process for use in the detection of biological substances, or for improving the detection of biological substances by amplification of the signal resulting from other techniques. For example, one commonly used marker substance used in the detection of biological substances is peroxidase, and the invention may be used to increase the sensitivity of such a detection technique. A further object of the invention is to provide a novel set or combination of materials, or a kit, for use in carrying out the procedure.

Broadly stated from one aspect the invention consists in a method for the detection of a biological substance of interest (optionally in an environment of biological cells) in which a marker substance is linked specifically, directly or indirectly, to the substance of interest, the marker substance being selected to act as a catalyst in a subsequent process of reduction of silver using a developing solution.

From another aspect the invention consists in a kit of parts for use in detecting a biological substance of interest, comprising a marker substance capable of being specifically linked with the substance of interest, and a catalyst capable of combining with the marker substance to catalyse subsequent reduction of silver using a developing solution. Thus from another aspect the invention consists in the identification and/or localization and/or quantification of biological substances by direct or indirect labelling with a sulphide of an exogenous element to catalyse the reduction of silver. Alternatively it may be seen as the labelling of a marker substance (e.g. DAB) with a second marker (e.g. gold) which is capable of conversion to an insoluble sulphide product, or differently stated it is based on the conversion of a marker substance to its sulphide to allow of subsequent silver deposition.

It will be understood that many modifications are possible within the broad scope of the invention. In place of techniques involving use of antibodies to link the marker substance directly or indirectly to the substance of interest other specific binding techniques may be used such as nucleic acid probes, or other specific probes such as lectins. The visualizing agent may consist of some alternative to DAB such as 4-chloro-1-naphthol, or 3-amino-9 ethyl-carbazole. The silver developing solution may likewise be varied, and the marker or label linked to the substance need not necessarily be an enzyme such as peroxidase or glucose oxidase.

Insoluble sulphides catalyse the reduction of silver salt solutions. If endogenous heavy metals are present in tissue, then when converted to a sulphide, the heavy metals form insoluble deposits which can be visualized by using them to precipitate reduced silver (silver metal). This catalytic property of sulphide is only expressed when it and the silver salt solution are in the presence of a reducing agent. Unfortunately light is also a catalytic agent so that when a silver salt is mixed with a reducing agent in daylight a precipitate of reduced silver is rapidly produced in the solution which turns black. The catalytic effect of light can be drastically reduced by including tungstosilicic acid in the silver salt/reducer solution, but surprisingly it has now been discovered that the inclusion of tungstosilicic acid does not prevent the catalytic effect of sulphide so that by using a silver nitrate containing reducing solution, reduced silver can be deposited at the site of a sulphide in full daylight. It is possible to label biological substances, directly or indirectly, with artificially introduced sulphides. This provides an entirely original means by which to identify, localize and quantify biological substances using a silver salt containing reducing solution such as that described above.

A sulphide-silver method according to the invention can be used to advantage in immunocytochemistry. Biological substances (antigens) can be visualized in tissue sections by reacting them with labelled antibodies. A commonly used label is the enzyme peroxidase which uses hydrogen peroxide as its substrate. Diaminobenzidine (DAB) when in solution in the presence of peroxidase and hydrogen peroxide is caused to precipitate by the action of the peroxidase enzyme so that wherever the enzyme reaction occurs a red-brown deposit of DAB will result. Often this coloured precipitate is enough to enable the reaction to be visualized microscopically and it marks the site of antibody/antigen binding. Thus, for example, the distribution of a hormone in a tissue section can be demonstrated by using an antibody to the hormone labelled directly or indirectly with peroxidase. In practice, the sensitivity of such a system is limited by the low optical density of DAB when it is deposited in small amounts. The sulphide silver method, however, can overcome this problem. DAB has a high affinity for gold salts so that it will readily take up gold chloride from its solution in water. In turn the DAB/gold chloride can be converted to its sulphide by using an aqueous solution of sodium sulphide. The DAB/gold sulphide now forms an efficient base on to which reduced silver can be increasingly deposited until a point is reached where the DAB/gold sulphide/silver reaction product is clearly visible microscopically.

Many types of techniques are currently used for the identification and/or localization and/or quantification of a wide variety of biological substances. Examples include identification and/or localization and/or quantification of antigens in tissues, discussed above, the identification and/or localization and/or quantification of enzymes in tissues, the identification and/or localization and/or quantification of carbohydrates in tissues using lectins, the identification and/or localization and/or quantification of nucleic acids in tissues using nucleic acid probes, the identification and/or localization and/or quantification of tissue products such as nucleic acids, carbohydrates, etc., on artificial substrates such as polyacrylamide gels, nitrocellulose paper, and other materials used for the separation of tissue extracts into their constituent substances. The methods used commonly employ a label, and the procedure described here has wide applications to increase the sensitivity of identification, localization and quantification of these substances whatever the primary probe used.

The sulphide-silver method can be tested using a simple model. Diaminobenzidine (DAB) solution is directly dried on to nitrocellulose filter paper. Before use the filter paper should be washed for 5-10 minutes in distilled water and allowed to air-dry. 3 μl droplets of decreasing concentrations of DAB are spotted on to 5 mm² pieces of the pretreated nitrocellulose and air-dried for 60 minutes. Six 5-fold reductions in concentration from 0.1% DAB to 0.00032% DAB provides a useful dilution profile on which to observe the silver reaction. Each piece of nitrocellulose with its spot of dried DAB is immersed in 0.1% gold chloride for 5 minutes. They are then washed in three changes of distilled water for 1 minute each change before being immersed in 0.5% sldium sulphide (100 ml sodium sulphide neutralized with 2.8 ml NHCl) for 5 minutes. After three more 1 minute washes in distilled water the DAB 'blots' are 'developed' in silver reducing solution for 10 minutes. The reaction is stopped by immersing the 'blots' in droplets of 1% acetic acid after which they can be left to dry. All operations are conducted at room temperature and in full daylight. The silver reduction solution can be as follows:

Stock solution A
5% Sodium carbonate (anhydrous)
Stock solution B
0.2 g Ammonium nitrate
0.2 g Silver nitrate
1.0 g Tungstosilicic acid
100.0 ml Distilled water The constituents of B which also includes a proportion of formaldehyde must be dissolved in the order shown. The silver reducing solution should be freshly prepared for use by adding 1 volume of A to 1 volume of B. It will remain quite clear for over 1½ hours in normal daylight.

What is claimed is:

1. A method of detecting or quantifying a substance of biological interest in which a peroxidase enzyme marker substance is specifically linked with said substance of interest, the peroxidase is reacted with a visualizing agent selected from the group consisting of (a) diaminobenzidine, (b) 4-chloro-1-naphthol, and (c) amino-9-ethyl-carbazole, the product of the visualizing agent/peroxidase reaction is reacted with a gold salt and with a sulphide salt, and the gold sulphide reaction product is then included as a catalyst in a further reaction with a silver developing solution to precipitate reduced silver.

2. A method according to claim 1, in which the gold salt is gold chloride.

3. A method according to claim 2, in which the sulphide salt is sodium sulphide.

4. A method according to claim 3, in which the sodium sulphide is neutralized.

5. A method according to claim 1, in which the visualizing agent is diaminobenzidine.

6. A method according to claim 1, in which the silver developing solution includes tungstosilicic acid.

7. A method according to claim 1, in which the marker substance is capable of forming a specific immunological bond with the substance of interest.

8. A method according to claim 7, in which the biological substance of interest is an antigen, and the marker substance includes a specific antibody thereto.

9. A method according to claim 1, in which the substance of interest includes nucleic acid and the marker substance comprises a mucleic acid probe and capable of linking specifically with the nucleic acid.

10. A method according to claim 1, in which the substance of interest includes a carbohydrate, and the marker substance includes a lectin, capable of specifically linking with the carbohydrate.

11. A kit for use in detecting a substance of biological interest, comprising a marker substance capable of being specifically linked with the substance of biological interest, and said marker substance including peroxidase enzyme, a visualizing agent for said peroxidase selected from the group consisting of diaminobenzidine, chloro-1-naphthol, and amino-9-ethyl-carbazole, and a visualizing enhancing system comprising a solution of gold salt, a solution of a sulphide salt, and a final silver developing solution.

12. A kit according to claim 11, in which the gold salt is gold chloride.

13. A kit according to claim 11, in which the sulphide salt is sodium sulphide.

14. A kit according to claim 11, in which the visualizing agent is diaminobenzidine.

15. A kit according to claim 11, in which the marker substance is capable of forming a specific immunological bond with the substance of interest.

16. A kit according to claim 11, in which the biological substance of interest is an antigen, and the marker substance includes a specific antibody thereto.

17. A kit according to claim 11, in which the substance of interest includes nucleic acid and the marker substance comprises a nucleic acid probe and capable of linking specifically with the nucleic acid.

18. A kit according to claim 11, in which the substance of interest includes a carbohydrate, and the marker substance includes a lectin, capable of specifically linking with the carbohydrate.

* * * * *